US010851867B2

(12) United States Patent
Pathak et al.

(10) Patent No.: US 10,851,867 B2
(45) Date of Patent: Dec. 1, 2020

(54) METHOD AND SYSTEM FOR A FEEDBACK CONTROLLER FOR A HANDHELD TOOL

(71) Applicant: Verily Life Sciences LLC, Mountain View, CA (US)

(72) Inventors: Anupam J. Pathak, Mountain View, CA (US); Dylan Owens, Sunnyvale, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 1050 days.

(21) Appl. No.: 15/249,844

(22) Filed: Aug. 29, 2016

(65) Prior Publication Data
US 2018/0058536 A1 Mar. 1, 2018

(51) Int. Cl.
G05B 6/02 (2006.01)
F16F 15/00 (2006.01)
(Continued)

(52) U.S. Cl.
CPC ............ F16F 15/005 (2013.01); A47G 21/04 (2013.01); A61B 5/1101 (2013.01);
(Continued)

(58) Field of Classification Search
CPC ......... F16F 15/005; A47G 21/04; G05B 5/01; G05B 6/02
(Continued)

(56) References Cited

U.S. PATENT DOCUMENTS 3,918,309 A 11/1975 O'Connor et al.
6,234,045 B1 5/2001 Kaiser
(Continued)

FOREIGN PATENT DOCUMENTS

| CN | 103906483 A | 7/2014 |
| JP | 2008067936 A | 3/2008 |
| WO | 2016133621 A1 | 8/2016 |

OTHER PUBLICATIONS

"How to use Liftware", Liftware, <https://www.liftware.com/how/>, Mar. 5, 2016.
(Continued)

Primary Examiner — Kawing Chan
(74) Attorney, Agent, or Firm — Christensen O'Connor Johnson Kindness PLLC

(57) ABSTRACT

Systems and methods for tracking unintentional muscle movements of a user and stabilizing a handheld tool while it is being used are described. The method may include measuring, with a first inertial measuring unit ("IMU"), at least an orientation of a housing of the handheld tool, and measuring, with a second IMU, at least an orientation or an attachment arm extending from the housing of the handheld tool. The method may also include storing the orientation of the housing and the orientation of the attachment arm in a memory. Furthermore, the method may include controlling, with a processing logic, a first motion generating mechanism and a second motion generating mechanism to move the attachment arm relative to the housing based on the measured orientation of the housing and the measured orientation of the attachment arm to stabilize motion of a user-assistive device attached to a distal end of the attachment arm.

20 Claims, 7 Drawing Sheets

(51) Int. Cl.
*A61B 5/11* (2006.01)
*A61B 5/00* (2006.01)
*A47G 21/04* (2006.01)
*G05B 5/01* (2006.01)
*A47G 21/02* (2006.01)
*A61B 34/00* (2016.01)
*G01C 21/18* (2006.01)
*A61F 2/50* (2006.01)

(52) U.S. Cl.
CPC .......... *A61B 5/1114* (2013.01); *A61B 5/4082* (2013.01); *A61B 5/4836* (2013.01); *A61B 5/6887* (2013.01); *F16F 15/002* (2013.01); *G05B 5/01* (2013.01); *G05B 6/02* (2013.01); *A47G 21/02* (2013.01); *A47G 2200/046* (2013.01); *A61B 5/0022* (2013.01); *A61B 34/75* (2016.02); *A61B 2562/0219* (2013.01); *A61F 2002/5003* (2013.01); *A61F 2002/5018* (2013.01); *A61F 2002/5033* (2013.01); *G01C 21/18* (2013.01)

(58) Field of Classification Search
USPC .......................................................... 318/648
See application file for complete search history.

(56) References Cited

U.S. PATENT DOCUMENTS

| | | | | |
|---|---|---|---|---|
| 10,159,428 | B1* | 12/2018 | Shoeb .................. | A61B 5/1101 |
| 2008/0284650 | A1* | 11/2008 | MacIntosh ......... | A63B 24/0021 |
| | | | | 342/357.57 |
| 2010/0145236 | A1* | 6/2010 | Greenberg ........... | A61B 5/1101 |
| | | | | 600/595 |
| 2010/0228362 | A1 | 9/2010 | Pathak et al. | |
| 2012/0086725 | A1* | 4/2012 | Joseph .................. | G06F 3/0346 |
| | | | | 345/629 |
| 2013/0033205 | A1* | 2/2013 | Furukawa ........... | H02P 21/0003 |
| | | | | 318/400.02 |
| 2013/0297022 | A1 | 11/2013 | Pathak | |
| 2014/0052275 | A1 | 2/2014 | Pathak | |
| 2014/0288896 | A1* | 9/2014 | Li .......................... | G06F 30/20 |
| | | | | 703/2 |
| 2014/0303605 | A1 | 10/2014 | Boyden et al. | |
| 2015/0054633 | A1 | 2/2015 | Saddik et al. | |
| 2015/0300394 | A1 | 10/2015 | Pathak | |
| 2016/0242679 | A1 | 8/2016 | Pathak et al. | |
| 2017/0348127 | A1* | 12/2017 | Pathak ................. | A61B 5/1121 |
| 2018/0014958 | A1* | 1/2018 | Pathak ................. | A61B 5/6887 |

OTHER PUBLICATIONS

"Gyenno Spoon for Hand Tremors," Pozible, <http://www.pozible.com/project/196012>, Jan. 20, 2016.
Allen, Brian, "'Smart' Spoon Allows Parkinson's Sufferers to Feed Themselves," News/Science & Technology, <https://www.voanews.com/content/smar-spoon-allows-parkinsons-suffers-to-feed-themselves/1832017.html>, Jan. 21, 2014.
U.S. Appl. No. 14/627,893; Anupam Pathak; filed Feb. 20, 2015.
U.S. Appl. No. 14/668,516; Anupam Pathak; filed Mar. 25, 2015.
U.S. Appl. No. 14/681,549; Anupam Pathak; filed Apr. 8, 2015.
U.S. Appl. No. 13/250,000; Anupam Pathak; filed Sep. 30, 2011.
U.S. Appl. No. 15/210,267; Aunpam Pathak; filed Jul. 14, 2016.
PCT/US2016/065941 International Search Report and Written Opinion of the International Searching Authority, dated May 24, 2017, 9 pages.
Chinese Office Action, with English Translation, dated Feb. 3, 2020, in corresponding Chinese Patent Application No. 201611262684.8, 38 pages.
Chinese Office Action, dated Sep. 27, 2020, in corresponding Chinese Patent Application No. 201611262684.8, 18 pages.

* cited by examiner

METHOD AND SYSTEM FOR A FEEDBACK CONTROLLER FOR A HANDHELD TOOL

TECHNICAL FIELD

This disclosure relates generally to unintentional muscle movements, and in particular but not exclusively, relates to tracking unintentional muscle movements of a user and stabilizing a handheld tool while it is being used by the user.

BACKGROUND INFORMATION

Movement disorders are often caused by chronic neurodegenerative diseases such as Parkinson's Disease ("PD") and Essential Tremor ("ET"). Both of these conditions are currently incurable and cause unintentional muscle movements or human tremors—uncontrollable rhythmic oscillatory movements of the human body. In many cases human tremors can be severe enough to cause a significant degradation in quality of life, interfering with daily activities/tasks such as eating, drinking, or writing.

Currently, persons with chronic neurodegenerative diseases are typically medicated with drugs that vary in effectiveness. The alternative to pharmacological treatment is brain surgery, such as deep brain stimulation (DBS) surgery. Similar to pharmacological treatments, DBS surgery varies in its effectiveness while being invasive and dangerous. Both forms of treatment are therefore non-optimal for treating persons with chronic neurodegenerative diseases, especially with respect to performing daily activities.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus, system, and process for tracking unintentional muscle movements of a user while using a handheld tool and stabilizing the handheld tool while the handheld tool is used to perform an ordinary activity, are described herein. In one embodiment, stabilization of the handheld tool is performed based on one or more measured orientations of the handheld tool. In addition to stabilization, in embodiments, parts of the handheld tool may be aligned based on the one or more measured orientations of the handheld tool to prevent drifting of the parts away from an expected orientation of the parts relative to one another. In embodiments, the stabilization and orientation maintenance may both be performed based on the one or more measured orientations of different parts of the handheld tool in order to provide a computationally and power efficient motion stabilization system. Furthermore, by utilizing measured orientations of the handheld tool, the mechanical design of the handheld tool can be simplified therefore enabling a more robust construction of the handheld tool.

In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment", "an embodiment" or similar, means that a particular feature, structure, or characteristic described in connection with the embodiment may optionally be included in at least one embodiment of the present invention. Thus, the appearances of the phrases "in one embodiment", "in an embodiment" or similar in various places throughout this specification are not necessarily all referring to the same embodiment. Furthermore, the particular features, structures, or characteristics may be combined in any suitable manner in one or more embodiments.

Figure 1:
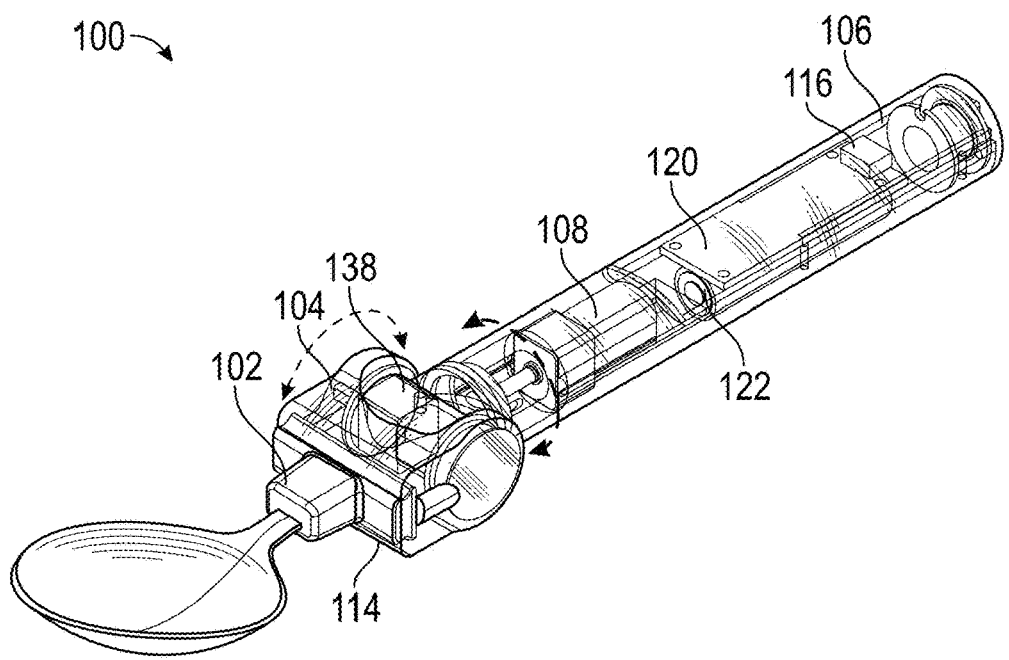
FIG. 1 is a perspective view illustration of a handheld tool that tracks unintentional muscle movements and performs motion stabilization based on one or more measured orientations of the handheld tool, in accordance with an embodiment of the disclosure.

FIG. 1 is a perspective view illustration of a handheld tool 100 that tracks unintentional muscle movements and performs motion stabilization based on one or more measured orientations of the handheld tool. In one embodiment, handheld tool includes a housing 106 (e.g., a handle) coupled with an attachment arm 104. Furthermore, the attachment arm 104 may have an implement 102 detachably attached thereto. In one embodiment, the housing 106 and attachment arm 104 are discrete rigid bodies of the handheld tool 100 connected by rotary joints enabling movement of the attachment arm 104, and thus the implement 102, in two degrees of freedom relative to the housing 106. Handheld tool 100 is capable of detecting and compensating for unintentional muscle movement (e.g. tremors). In embodiments discussed herein, the handheld tool 100 may track these unintentional muscle movements, and stabilize and center a position of implement 102 in spite of unintentional muscle movements while the handheld tool 100 is being held and used by a user.

Accordingly, the illustrated embodiment of handheld tool 100 may include a tremor tracking module 120 for measuring and tracking user tremors, as well as two or more sensors (e.g., sensor 116 and 114) for providing signals to the tremor tracking module 120 for compensating for those same tremors, as discussed herein. In one embodiment, the signals may include data that enables tremor tracking module 120 to measure an orientation of the handle 106, an orientation of the attachment arm 104, and thus the relative orientations there between as well as orientations relative to an absolute orientation. These subsystems may have distinct components, or share some components such as power systems, memory, and may even share one or more sensors.

Handheld tool 100 includes a housing 106, which functions as a handle enabling a user to hold handheld tool 100. Handheld tool 100 also includes an attachment arm 104 coupled to the housing 106 via motion generating mechanisms, as discussed in greater detail below. Attachment arm 104 is configured to accept an implement 102 (e.g., a user-assistive device, such as a spoon in the illustrated embodiment) to its end distal from housing 106. In one embodiment, attachment arm 104 is integrated with a specific type of implement 102 (e.g., the spoon as illustrated). In other embodiments, attachment arm 104 can receive a variety of different implements 102 in a variety of ways including but not limited to a friction, snap, magnet, screw, or other form of locking mechanism.

Handheld tool 100 may include tremor tracking module ("TTM") 120 for measuring and tracking tremors, such as unintentional muscle movements of a user, as well as for controlling stabilization performed by the handheld tool using a first motion generating mechanism 108 (e.g., one or more of an actuator, a gear reduction unit, and a rotary gearing unit) and a second motion generating mechanism 138 (e.g., one or more of an actuator, a gear reduction unit, and a rotary gearing unit). In embodiments, the attachment arm 104 may be coupled with the housing 106 via the coupling of the first motion generating mechanism 108 with the attachment arm 104 and the first motion generating mechanism 108 may control movement of the attachment arm 104 in a first degree of freedom about an axis of the housing 104. FIG. 2B illustrates movement 240 in the first degree of freedom 242. In embodiments, the second motion generating mechanism 138 may control motion of the attachment arm 104 in a second degree of freedom perpendicular to the axis of the housing. FIG. 2C illustrates movement 250 in the second degree of freedom 252.

In embodiments, one or more components of TTM 120 may be rigidly attached to housing 106 to measure and track tremors of the handle that the user holds. FIG. 1 illustrates TTM 120 as a single component within housing 106; however, in other embodiments, TTM 120 includes several functional items that may assume a variety of different form factors and may further be spread throughout housing 106, such as within attachment arm 104.

The illustrated embodiment of handheld tool 100 further include at least two motion sensors (e.g., a first motion sensor 116 placed along or within housing 106 and a second motion sensor 114 placed along or within attachment arm 104). In one embodiment, each of the first motion sensor 116 and second motion sensor 114 are inertial measuring units (IMUs) capable of providing measurements of orientations, angular rate of movement, force, etc. of the bodies in which they are placed. In one embodiment, each IMU is a six degree of freedom IMU having at least an accelerometer and a gyroscope. In one embodiment, the motion sensors 116 and 114 respectively collect measurements during use of the handheld tool 100 to determine an orientation of the housing 106 and attachment arm 104.

Figure 2A:
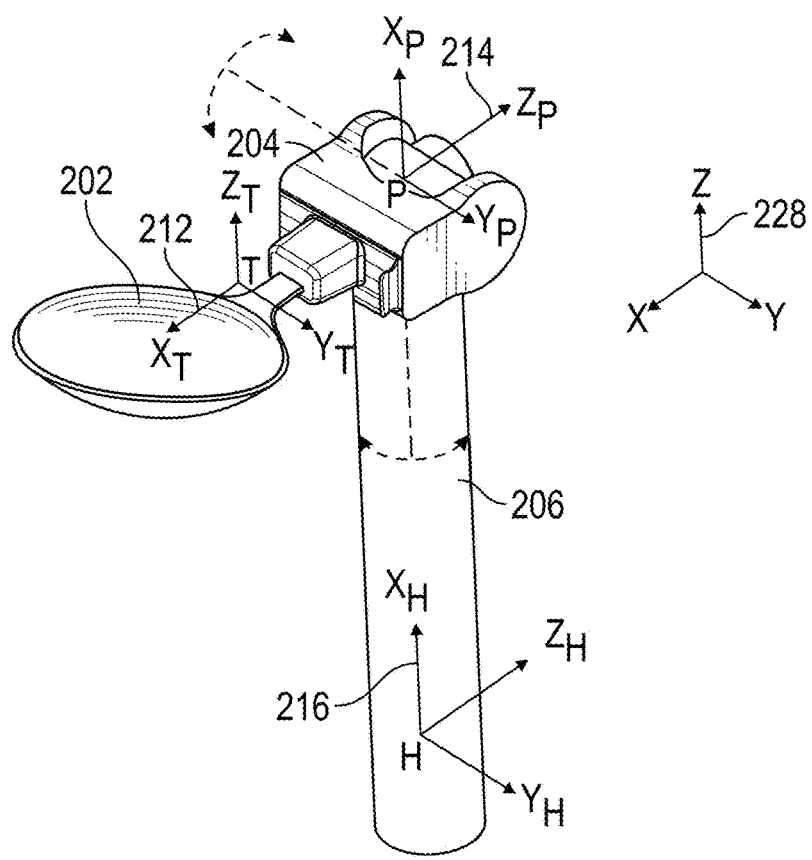
FIG. 2A is a perspective view illustration of a handheld tool and reference orientations of parts of the handheld tool, in accordance with an embodiment of the disclosure.
Figure 2B:
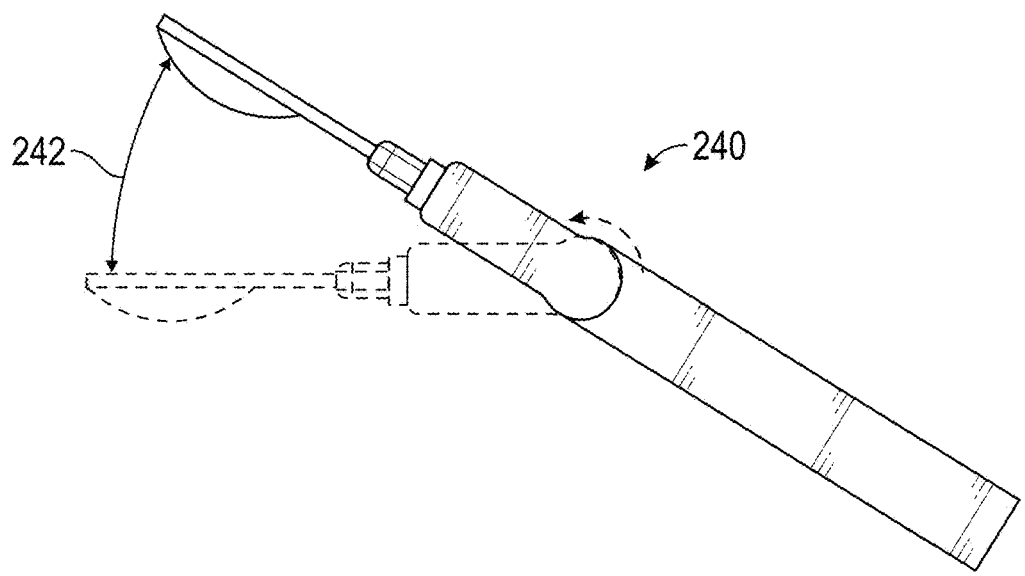
FIG. 2B is a perspective view illustration of a first type of motion of the handheld tool that performs motion stabilization, in accordance with an embodiment of the disclosure.
Figure 2C:
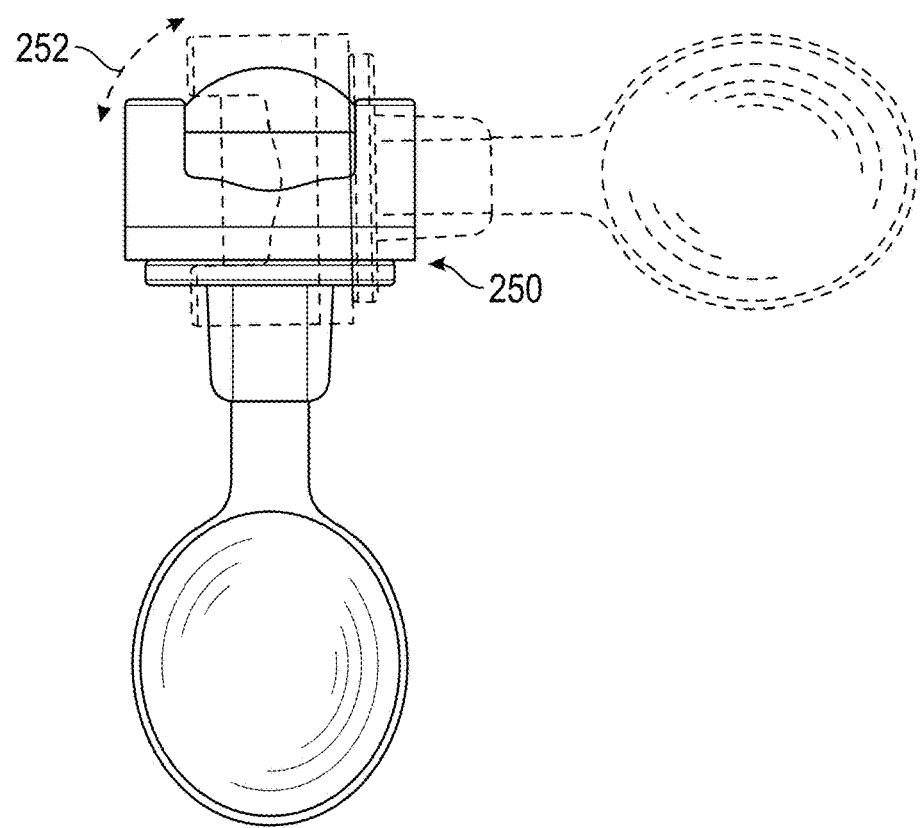
FIG. 2C is a perspective view illustration of a second type of motion of the handheld tool that performs motion stabilization, in accordance with an embodiment of the disclosure.

FIG. 2A illustrates handheld tool 200 and potential orientations of the handle 206, attachment arm 204, and implement 202 during use. A reference frame 216 (e.g., $x_h$, $y_h$, $z_h$ measurement(s)) indicative of the orientation of housing 206 may be obtained by measurements collected from sensor 116. Similarly, reference frames 212 (e.g., $x_t$, $y_t$, $z_t$ measurement(s)) and 214 (e.g., $x_p$, $y_p$, $z_p$ measurement(s)) indicative of orientation of the implement 202 and attachment arm 214, respectively, may be obtained by measurements collected from sensor 114. In the illustrated embodiment, the orientation of the reference frames are fixed within each part of the handheld tool 200, with each having an x, y, and z component that, based on a measured orientation, provide an indication of the relative orientation of the part of the handheld tool 200 in comparison to an absolute orientation 228 in space. For example, the absolute orientation 228 may have a z component that is directed to true North, or up, based on earth's gravitational force (e.g., $z_e$). Thus, $z_t$ can be compared to $z_e$, and operations performed to ensure that $z_t$ matches $z_e$ during use of the handheld tool maintain and stabilize implement in an upward orientation regardless of unintentional movements of a user. The process for maintaining this orientation is discussed in greater detail below.

In one embodiment, the geometry/construction of handheld tool 200, and similarly handheld tool 100, establishes several orientation rules between the parts of the handheld tool 200. That is, there are expected relationships between the orientations of the parts of the handheld tool 200. For the illustrated embodiment of the handheld tool, $y_t$ and $x_h$ should be perpendicular, $y_t$ and $p_t$ should be parallel, and $x_p$ and $x_h$ should be parallel. When any of these expected relationships is not correct, then the tool is misaligned and TTM 120 can control motion of the misaligned parts to correct the orientations by bringing them back into alignment. The correction process is discussed in greater detail below.

Although certain expected relationships between parts of the handheld tool 200 are described and illustrated, these expected relationships are based on the construction and resulting relative geometric relationships of the different parts of the handheld tool. Other constructions, geometries, and/or shapes that have expected relationships and/or relationships between parts and desired orientations may utilize the techniques for orientation control and maintenance discussed herein.

Returning to FIG. 1, the illustrated embodiment of handheld tool 100 includes at least one sensor 114, such as an IMU placed along or within attachment arm 104 to measure movement of attachment arm 104, and another sensor 116, such as an IMU placed along or within housing 106 to measure movement of the housing 106. As discussed herein, the measurements collected by sensors 114 and 116 may include data indicative of an orientation, angular speed, force, etc., of the corresponding part of the handheld tool 100. In one embodiment, the sensors 114 and 116 send motion data (e.g., measured orientations, angular velocities, etc.) to TTM 120.

In embodiments, handheld tool 100 may further include a portable power source 122 to power the TTM 120 and the motion generating mechanisms (e.g., 108 and 138). Power source 122 may utilize a variety of options including but not limited to a rechargeable battery, a solar panel, etc. In one embodiment, attachment arm 104 is integrated with a specific type of implement 102 (e.g., a spoon as illustrated). In other embodiments, attachment arm 104 may be configured to receive a variety of different implements 102 in a variety of ways including but not limited to a friction, snap, or other form of locking mechanism.

The sensor 114 and sensor 116 take measurements to determine an orientation of the housing 106 and an orientation of the attachment arm 104 and/or implement 102. TTM 120, based on these two orientations, can determine the relative orientations of the parts of the handheld tool 100. Furthermore, relative orientations of the parts TTM 120 can determine the position of the joints that couple the housing 106 with the attachment arm 104 and the current orientation of the attachment arm 104, and thus the implement 102, relative to the housing 106. As will be discussed in greater detail below, based on the measured orientations and expected orientations between parts of the handheld tool 100, the TTM 120 may generate motor commands for the motion generating mechanisms that correct and/or maintain an expected orientation between the different parts of the handheld tool 100 to, for example, to prevent implement 102 from unintentionally drifting away from an initial orientation relative to the housing 106. Furthermore, TTM 120 can also use the measured orientations to generate motor commands for the motion generating mechanisms that correct for adverse unintentional user motions during use of the handheld tool 100. In one embodiment, the motor commands may include voltage commands generated by TTM 120 that drive the actuators of the motion generating mechanisms 108 and 138 to turn their respective gears in a desired direction, at a desired speed, with a desired acceleration, etc. For example, if implement 102 is a spoon, the spoon should be maintained in an upward orientation to ensure food within the spoon is not spilled when used by a user. In embodiments, based on the measured orientation of implement 102 (e.g., $z_t$) and a desired orientation (e.g., up, or opposite earth's gravitational force, $z_e$), TTM 120 can generate the motor commands for the motion generating mechanisms 108 and 138 that moves the implement's 102 current orientation in the direction of the desired orientation. In embodiments, these orientations may be determined from the measurements of the sensors 114 and 116, and not from physical sensors attached to gearing of the motion generating mechanism. As a result, the design and construction of the motion stabilizing handheld tool 100 can be simplified. Furthermore, by reducing the number of different components that utilize power source 122, the operation of handheld tool 100 is made more energy efficient. Finally, as discussed in greater detail below, the use of orientation measurements of the different parts of the handheld tool may enable a computationally efficient process for maintaining correct alignment of parts of the handheld tool 100, as well as for correcting for unintentional user movements by maintaining one or more desired orientations of parts of the handheld tool 100.

One of ordinary skill in the art readily recognizes that a system and method in accordance with the present disclosure may utilize various implementations of TTM 120, sensors 114 and 116, motion generating mechanisms 108 and 138, etc. that would be within the spirit and scope of the present disclosure. In one embodiment, TTM 120 comprises an electrical system capable of producing an electrical response from sensor inputs such as a programmable microcontroller a field-programmable gate array (FPGA), an application specific integrated circuit ("ASIC"), or otherwise. In one embodiment, TTM 120 comprises an 8-bit ATMEGA8A programmable microcontroller manufactured by Atmel due to its overall low-cost, low-power consumption and ability to be utilized in high-volume applications.

One of ordinary skill in the art will readily recognize that an apparatus, a system, or method as described herein may be utilized for a variety of applications. For example, various different implements 102 may include a manufacturing tool, a surgical tool, a kitchen utensil (e.g., fork, knife, spoon), a sporting tool, a yard tool, a grooming tool (e.g., comb, nail clippers, tweezers, make-up applicator, etc.), or a dental hygiene tool (e.g., toothbrush, flossing tool, etc.). Thus, handheld tool 100 may be useful in not only improving the quality of life for the multitudes of individuals suffering from neurological motion disorders, but also in assisting in a variety of applications where physiological tremor is an issue including but not limited to manufacturing, surgical and public safety applications.

Figure 3:
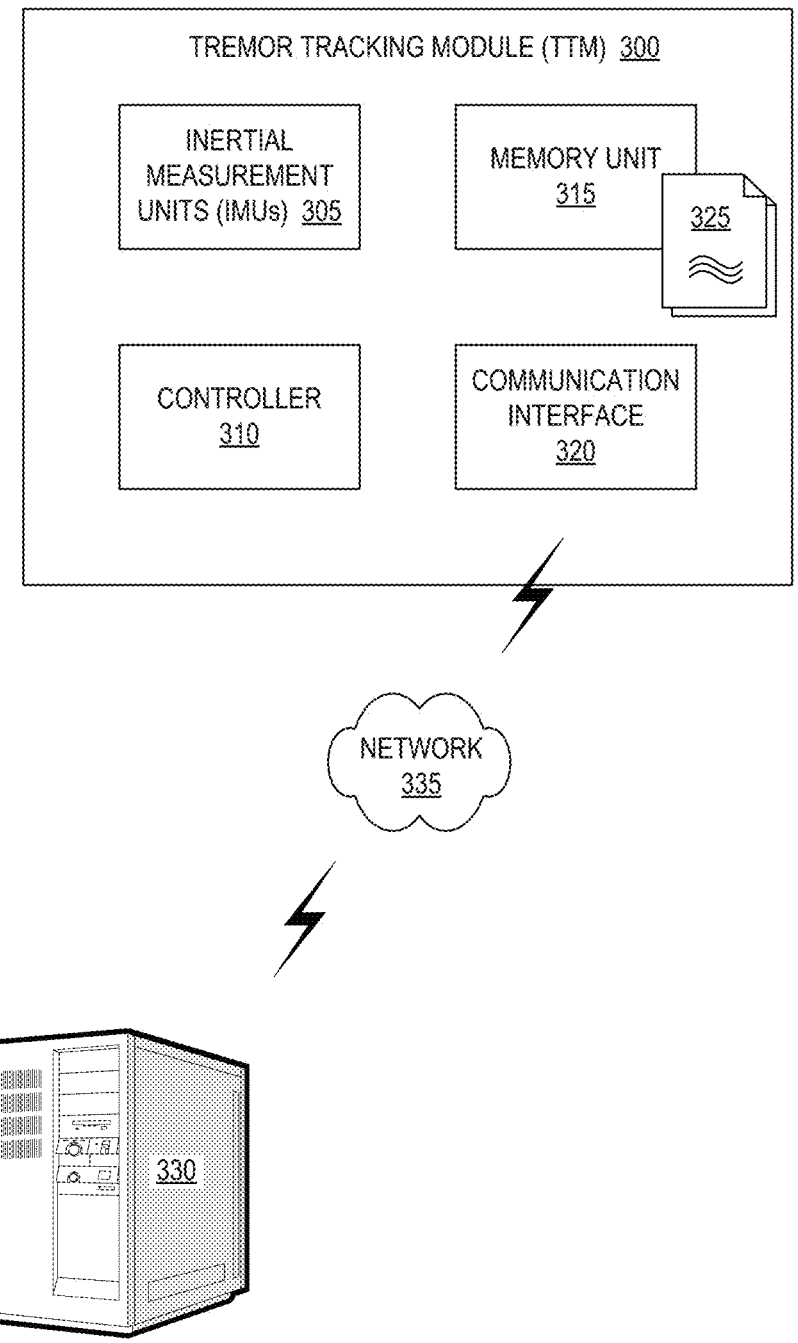
FIG. 3 is a functional block diagram illustrating a tremor tracking module, in accordance with an embodiment of the disclosure.

FIG. 3 is a functional block diagram illustrating a TTM 300, in accordance with an embodiment of the disclosure. TTM 300 is one possible implementation of TTM 120 illustrated in FIG. 1. The illustrated embodiment of TTM 300 includes two inertial measurement unit ("IMUs") 305, a controller 310, a memory unit 315, and a communication interface 320.

In one embodiment, IMUs 305 are disposed in rigid contact with the housing and attachment arm of a handheld tool to directly measure the motions and orientations of the handle and attachment arm, and by extension, the tremor motions of the user's hand. TTM 300 facilitates the measurement of human tremors while a user is performing an everyday task, such as eating or grooming (e.g., applying makeup). This is an important distinction over conventional in-clinic evaluations that simply measure the tremor of a hand that a patient is attempting to hold steady. Measurement and tracking of tremors while the patient is performing an everyday task measures the condition under real-world scenarios that are most adversely impacted by human tremors. Accordingly, TTM 300 can be embedded within everyday items or tools that are used routinely by patients to accurately measure and track their condition. This can lead to improved evaluations.

Not only can TTM 300 of a handheld tool measure and track human tremors during a routine task, but it can conveniently do so over a period of time to obtain a more reliable dataset for statistical analysis. Furthermore, the handheld tool including TTM 300 can be used at home where the user is more relaxed and under less stress than a formal evaluation in a practitioner's office. Data collection within the home environment along with larger datasets than can be obtained in-clinic, can provide more reliable data for evaluation of a patient's symptoms. Improved evaluation and diagnosis of the patient's tremors facilitate improved treatments and interventions of the various diseases and the conditions that cause human tremors.

IMUs 305 may be implemented using a variety of devices that measure motions of the handle of handheld tool 100. For example, IMU 305 may include one or more accelerometers that measure linear accelerations. In one embodiment, IMUs 305 include accelerometers capable of measuring translational accelerations of the handle in three orthogonal dimensions (e.g., x, y, and z dimensions). In one embodiment, IMUs 305 include a gyroscope to measure rotational motions (e.g., angular velocity about an axis) of the handle of handheld tool 100. In various embodiments, the gyroscope may be capable of measuring the rotational motions about one, two, or three orthogonal rotational axes. In one embodiment, IMUs 305 include a magnetometer to measure motions of the handle relative to a magnetic field (e.g., Earth's magnetic field or other externally applied magnetic field). In various embodiments, IMUs 305 may include various combinations of some or all of the above listed motion measuring devices. Furthermore, these motion sensors may be disposed together on a common substrate that is rigidly attached to housing 106, or disposed throughout housing 106. In any of the embodiments of IMUs 305, an orientation of the part of the handheld tool to which it is attached may be derived or measured directly from the measurements of the corresponding IMU.

Controller 310 is communicatively coupled to IMUs 305 and memory unit 315 to read sensor data output from IMUs 305 and store motion and/or orientation data into memory unit 315. Motion data may be collected over a period of time. For example, motion data may be collected while the user performs an individual task, over the course of a day, a week, or other period of time. The collected motion data stored in memory unit 315 may form a motion log 325. In one embodiment, motion log 325 may contain enough information about the user's motions (linear accelerations, rotational velocities, durations of these accelerations/velocities, orientation relative to a magnetic field, etc.), based upon the motion data output from IMUs 305, to recreate those motions using motion log 325. In one embodiment, motion log 325 may also record date/time stamps of when the motion data was collected and/or may include one or more identifiers indicating the type of implement 102 that was attached to the handheld tool 100 when the motion data was collected. The type identifier may provide an indication of the activity (e.g., eating with a fork, knife, or spoon, etc.) being performed by the user when the motion data was collected. This activity information and time/date stamps may be useful for the practitioner when evaluating the patient's motion log 325 to determine if the patient's tremors correlate to particular activities or time of day. In yet other embodiments, motion log 325 may also record battery voltage as a function of date/time, which may be used to analyzing system performance and battery usage. Tracking battery voltage may be used as a sort of proxy for the amount of effort exerted by one or more of the actuators 108 and 138 to stabilize implement 102. As such, tracking battery voltage or battery consumption may correlate to the degree of a user's tremors since battery consumption will rise with increased tremors.

In one embodiment, controller 310 further provides motor commands in the way of voltage signals to the actuators of motion generating mechanisms 108 and 138 for controlling motion of implement 102. As discussed herein, the motor commands generated by controller 310 cause the actuator to move implement 102 via gears of one or more of the motion generating mechanisms 108 and 138 to, for example, maintain an expected orientation between parts of the handheld tool and to correct or move a part (e.g., implement 102) from a measured orientation to a desired orientation (e.g., maintaining a spoon implement in an upward orientation to prevent spilling during use, centering a position of the spoon, etc.). As discussed herein, the movement of implement 102 may occur with two degrees of freedom to correct for a wide array and magnitude of unintentional user movements.

Controller 310 may be implemented with a programmable microcontroller, an FPGA, an ASIC, or other devices capable of executing logical instructions. The logical instructions themselves may be hardware logic, software logic (e.g., stored within memory unit 315 or elsewhere), or a combination of both. Memory unit 315 may be implemented using volatile or non-volatile memory (e.g., flash memory).

Communication interface 320 may be communicatively coupled to output the motion log 325 from memory unit 315 to remote server 330 via network 335 (e.g., the Internet). In one embodiment, communication interface 320 is a wireless communication interface (e.g., Bluetooth, WiFi, etc.). For example, communication interface 320 may establish a wireless link to a user's cellular phone which delivers motion log 325 to server 330 via an installed tremor tracking application. The application may enable the user to control privacy settings, add comments about their usage of handheld tool 100, setup automatic periodic reporting of motion log 325, initiate a one-time reporting of motion log 325, determine a predominant pattern, direction, magnitude, etc. of unintentional muscle movements detected by TTM 300, along with other user functions. In yet another embodiment, communication interface 320 may be a wired communication port (e.g., USB port). For example, when the user connects handheld tool 100 to a charging dock to charge power source 122, communication interface 320 may also establish a communication session with remote server 330 for delivery of motion log 325 thereto.

Figure 4:
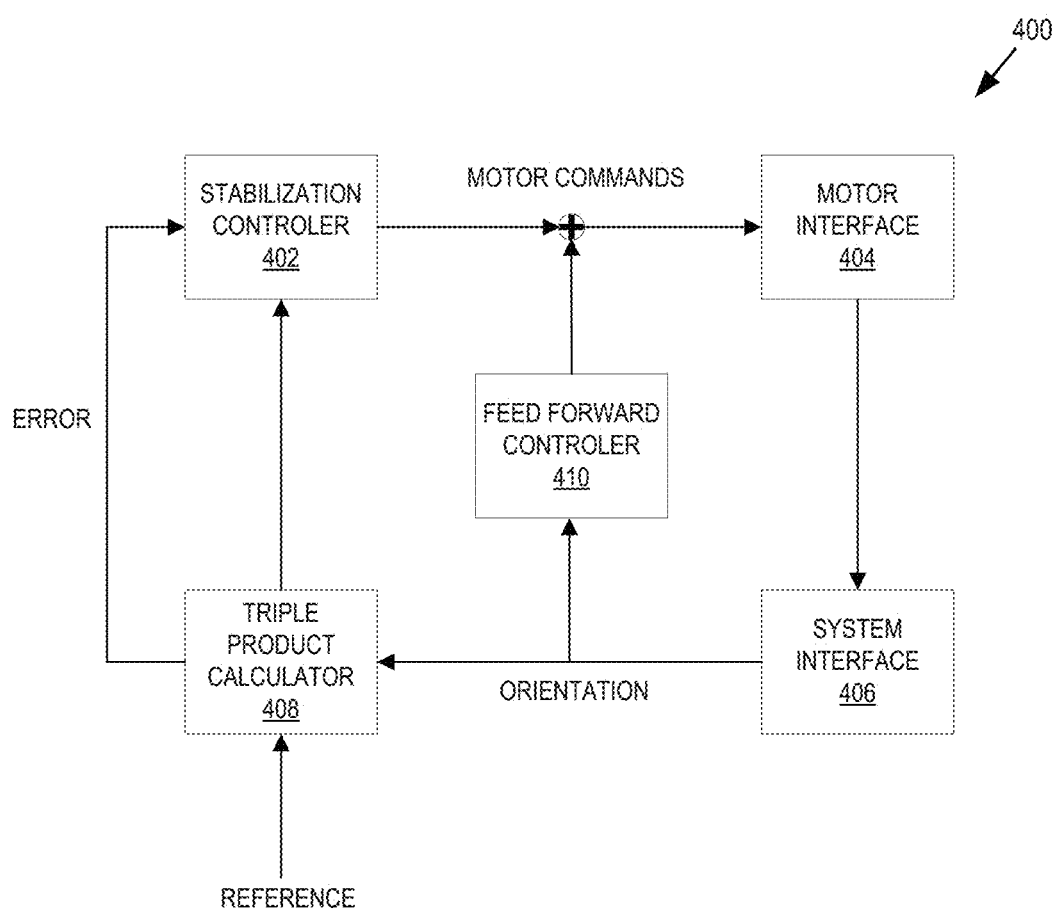
FIG. 4 is a functional block diagram illustrating a control loop for a handheld tool, in accordance with an embodiment of the disclosure.

FIG. 4 is a functional block diagram illustrating a control loop for a handheld tool, in accordance with an embodiment of the disclosure. The control loop 400 may be performed by processing logic that may comprise hardware (circuitry, dedicated logic, etc.), software (such as is run on a general purpose computer system or a dedicated machine), firmware, or a combination. In one embodiment, the control loop is performed by a controller of a tremor tracking module (e.g., controller 310) of a handheld tool. Furthermore, the order in which some or all of the control loop operations are performed should not be deemed limiting. Rather, one of ordinary skill in the art having the benefit of the present disclosure will understand that some of the control loop operations may be executed in a variety of orders not illustrated, such being executed in parallel.

In the illustrated embodiment of the control loop 400, system interface 406 collects the measurements taken by one or more IMUs of a handheld tool. For example, system interface 406 can collect periodic measurements, such as measurements taken in the range of 30-500 or more per second, from an IMU attached to or within a housing of a handheld tool, and an IMU attached to or within an attachment arm of a handheld tool. The measured orientations are then provided to the triple product calculator 408.

In one embodiment, triple product calculator 408 receives the measured orientations from system interface 406. Furthermore, triple product calculator may also receive, for example as a user preference value, preconfigured value, etc., a reference orientation. In one embodiment, the reference is one or more desired orientations of parts of the handheld tool. For example, the reference orientation can be an orientation opposite Earth's gravitation force as the desired orientation of an implement of handheld tool. Such a desired orientation would specify that the desired orientation of the implement is up to, for example, prevent tilting of the implement, spilling of content out of the implement, etc. As another example, the reference may also include expected relative orientations of different parts of a handheld tool. As discussed herein, those expected orientations are based on the construction/geometry of the handheld tool, and ensure proper alignment of the handheld tool during operation to, for example, prevent drift of the parts away from a proper alignment. As will be discussed in greater detail below, an error may be determined from the received measured orientations and the desired orientation and/or expected orientations. In embodiments, the error may be determined based on vector arithmetic, such as calculating dot products, calculating cross products, scaling vectors, etc. to determine an error vector representative of a target velocity and direction of movement of a given motion generating mechanism of a handheld tool that will correct for a current misalignment or change in orientation. In one embodiment, these can be referred to as joint velocities because the motion generating mechanisms move the handheld tool about the joints to which they are coupled. Each of the operations and computations that compute the error vectors will be discussed in greater detail in FIGS. 5-7 below. The error vector(s) may then be provided to stabilization controller 402.

Stabilization controller 402 may receive the error vectors/joint velocities computed by triple product calculator 408 and generate motor commands. In one embodiment, the motor commands are voltages that are to be supplied to actuators of handheld tool motion generating mechanisms. In one embodiment, based on known properties and characteristics of actuators of motion generating mechanisms (e.g., a voltage of X is needed to achieve joint velocity V, a voltage equation F(v) based on device characteristics is used to obtain voltage X given a desired joint velocity, direction, and acceleration, etc.), the voltages needed to achieve the desired speed and direction indicated by the error vectors is determined by stabilization controller 402.

In one embodiment, feed forward controller 410 may also be included in the control loop 400. In one embodiment, the feed forward controller 410 is responsible for generating motor commands that correct for disturbance motions of the handheld tool, such as rotations of the housing of the handheld tool. That is, the measurements of IMUs received by system interface 406 can include velocities, such as angular velocities, of the housing when moved by a user. Feed forward controller 410 may determine an error vector in the opposite direction of the movement (e.g., an opposite angular velocity), and then generate motor commands (e.g., actuator voltages) based on the error vector to cancel the detected movement. In one embodiment, control loop 400 adds the voltages determined by feed forward controller 410 with the voltages determined by stabilization controller 402 to generate a final set of motor commands. The final set of motor commands represent voltages to be applied to each motion generating mechanism to drive the associated motion generating mechanism's actuator. Motor interfaces 404 receive the motor commands (e.g., voltages) and apply the desired voltages to the respective motion generating mechanisms.

In embodiments, the desired voltages may drive each motion generating mechanism at a given speed, direction, acceleration, etc. to compensate for unintentional motions of a user, as detected by the IMUs measurements. In embodiments, the control loop 400 may be a periodic control mechanism that determines motor commands and drives motion generating mechanisms based on those commands in the range of 30-500 times per second. Because a user's motions, especially those with unintentional tremor motions, will in general be continually changing, the control loop's 400 periodic motor control may ensure the continual adaptation of the relative positions of parts of handheld tool to maintain the correct relative orientations (e.g., maintaining a handheld tool's implement facing upward) and the correct relative orientations (e.g., avoiding yaw drift of an implement away form an expected orientation) during use. Furthermore, triple product calculator 408, stabilization controller 402, and feed forward controller 410 may utilize computationally efficient techniques to determine error vector, calculate voltages, etc., so that a low power and limited capabilities processer can be used in the handheld tool. Beneficially, the processor can handle the periodic calculations at the desired periodicity without undue consumption of power from the handheld tools power source. Furthermore, the form factor needed to accommodate the processor can be minimized to provide a smaller handle/housing giving the resulting handheld tool a more familiar and user friendly shape.

Figure 5:
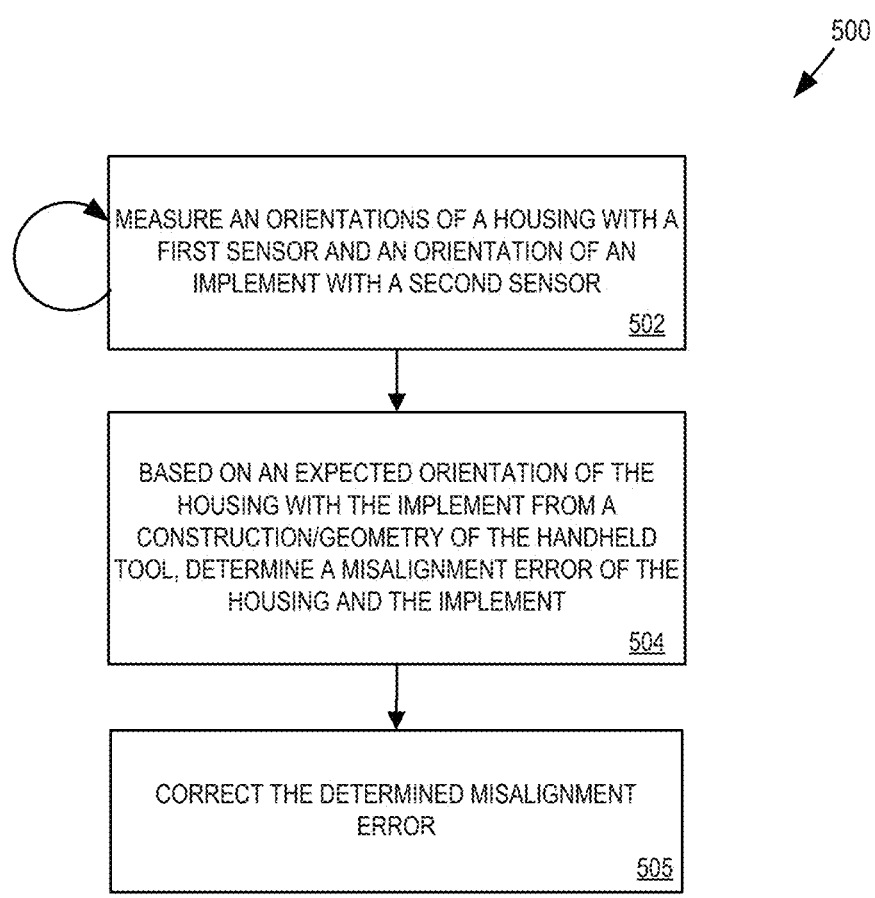
FIG. 5 is a flow chart illustrating a process for determining an error correction to an orientation of a handheld tool by inferring joint positions from one or more measured orientations of the handheld tool, in accordance with an embodiment of the disclosure.

FIG. 5 is a flow chart illustrating a process for determining an error correction to an orientation of a handheld tool by inferring joint positions from one or more measured orientations of the handheld tool, in accordance with an embodiment of the disclosure. The process 500 is performed by processing logic that may comprise hardware (circuitry, dedicated logic, etc.), software (such as is run on a general purpose computer system or a dedicated machine), firmware, or a combination. In one embodiment, the process is performed by a controller of a tremor tracking module of a handheld tool (e.g., controller 310, 400). Furthermore, the order in which some or all of the process blocks appear in process 500 should not be deemed limiting. Rather, one of ordinary skill in the art having the benefit of the present disclosure will understand that some of the process blocks may be executed in a variety of orders not illustrated, or even in parallel.

Processing logic may begin by periodically measuring an orientation of a housing with a first sensor and an orientation of an implement with a second sensor (processing block 502). As discussed herein, the sensors have a known orientation relative to their respective parts of the handheld tool, and enable different components of associated reference orientations (e.g., x, y, z) to be determined. In one embodiment, however, the measured orientations can drift relative to one another over time about a vertical axis regardless of motion of the housing and implement (e.g., the sensor readings can drift due to minor inherent error even when there is no motion). In embodiments, the known relative orientations of the respective parts may enable a correction of the orientations to be made by the controller before motion commands are generated, as discussed below in FIGS. 6 and 7.

Based on an expected orientation of the housing with the implement from a construction/geometry of the handheld tool, processing logic determines a misalignment error of the housing and the implement (processing block 504). One embodiment of a handheld tool was discussed above in FIGS. 1-2C. The expected orientation of the handheld tool can be defined based on certain expected relationships between the orientations of the different parts. In the illustrated embodiments of the handheld tool, certain axes of the handheld tool's different parts may be shared based on the construction/geometry of the device. For example, it may be expected that that the implement shares one axis with the attachment arm, the housing shares another axis with the attachment arm, and the implement axis is perpendicular to the housing axis. In the embodiment of the handheld tool illustrated in FIG. 2A, $y_t$ and $x_h$ should be perpendicular, $y_t$ and $p_t$ should be parallel, and $x_p$ and $x_h$ should be parallel. When any of these relationships are not satisfied by the sensor readings, a misalignment error has occurred (e.g., the shared axes are constant, and thus any detected misalignment in these axes represents an error). In one embodiment, processing logic determines the misalignment error from the sensor measurements by computing the dot product of both axes (e.g., $y_t$ and $x_h$) to determine how misaligned the relationship is. Processing logic may then scale the unit vector of one axis by this dot product, compute the cross product from the scaled vector with the unit vector of the other axis, and finally compute the dot product of the of the cross product result with the vertical vector to obtain a projection indicative of a correction that will cure the misalignment error (e.g., the non-existent misalignment that is due to sensor drift). Processing logic may use this projection to correct for the determined misalignment error (processing block 506). In one embodiment, the misalignment error is corrected by with a rotation of the relative orientations about the vertical axis proportional to the result from processing block 504.

In embodiments, the error correction discussed above may place the parts in a proper aligned state by correcting their relative orientations. The parts need not be moved with this error correction, as the error may be due to sensor drift and not actual movement of the parts relative to one another. In one embodiment, the misalignment error correction due to sensor drift ensures that when controller generates motor commands, as discussed herein, the commands are not applied to erroneous positions (e.g., positions inferred from incorrect starting orientations).

Figure 6:
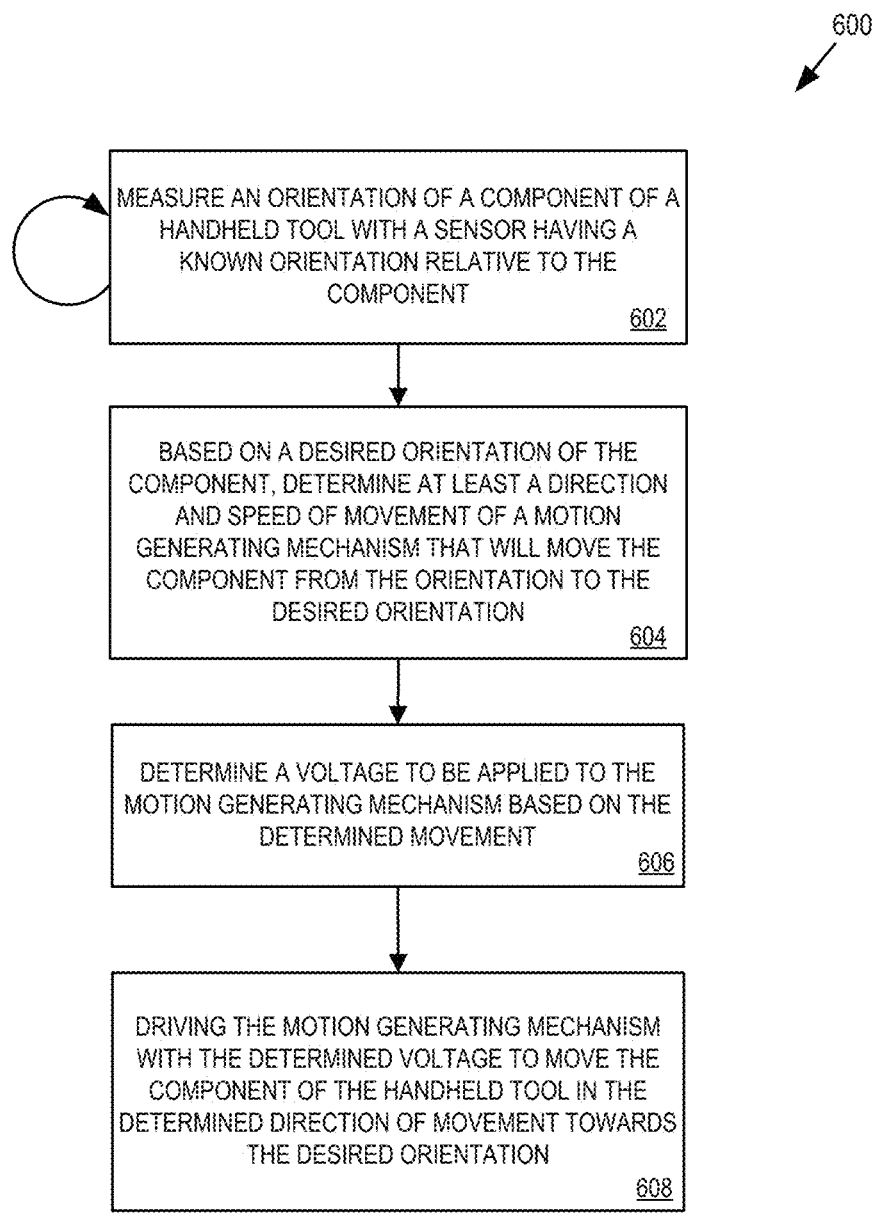
FIG. 6 is a flow chart illustrating a process for controlling stabilization of a handheld tool based on one or more measured orientations of the handheld tool, in accordance with an embodiment of the disclosure.

FIG. 6 is a flow chart illustrating a process 600 for controlling stabilization of a handheld tool based on one or more measured orientations of the handheld tool, in accordance with an embodiment of the disclosure. The process 600 may be performed by processing logic that may comprise hardware (circuitry, dedicated logic, etc.), software (such as is run on a general purpose computer system or a dedicated machine), firmware, or a combination. In one embodiment, the process is performed by a controller of a tremor tracking module of a handheld tool (e.g., controller 310, 400). Furthermore, the order in which some or all of the process blocks appear in process 600 should not be deemed limiting. Rather, one of ordinary skill in the art having the benefit of the present disclosure will understand that some of the process blocks may be executed in a variety of orders not illustrated, or even in parallel.

The process may begin by measuring an orientation of a component of a handheld tool with a sensor having a known orientation relative to the component (processing block 602). As discussed herein, the handheld tool (e.g., handheld tool 100) is a user assistive device that stabilizes motion of the component during unintentional muscle movements of a user. Furthermore, for example, the component of handheld tool may be an implement, such as a spoon, so that the sensor's measurement may be indicative of a current orientation of the spoon relative to an absolute orientation (e.g., an orientation based on earth's gravitation force). In one embodiment, the sensor may include more than one sensor, such as multiple IMUs capable of measuring angular velocities, force, etc. of different parts of the handheld tool.

Based on a desired orientation of the component, processing logic may determine at least a direction of movement of a motion generating mechanism that will move the component from the measured orientation to the desired orientation (processing block 604). In one embodiment, processing logic takes as an input the measure orientation in the form of a vector on component of the handheld tool representing a measured direction/orientation. Continuing the example above, the measured orientation can represent the present direction of the spoon's top face. The desired orientation may also be represented as a vector of a target direction—for example, straight up vertically relative to gravity. In one embodiment, processing logic calculates the cross product of the measured and target directions in order to produce a desired rotation vector in the direction of a rotation that would align the measured orientation with the desired orientation. The intermediate vector increases in magnitude as the misalignment between the measure orientation and the desired orientation grows. In one embodiment, processing logic computes a dot product of the desired rotation vector and unit vectors representing the rotational axes of each joint of the handheld tool. In one embodiment, the joints are the points of movement of the different parts of the handheld tool (e.g., where the housing 106 is joined with the attachment art 104 and moves in a first degree of freedom, and the attachment arm 104 moves in a second degree of freedom). These dot products represent the desired angular velocities of each joint. If the motion generating mechanisms are commanded to generate these angular velocities at each joint, the measured and target vectors (e.g., measured and desired orientations) can be aligned. Continuing the example, this would result in moving the motion generating mechanism such that the upward face of the spoon is aligned vertically relative to gravity. In one embodiment, unit vectors are utilized for the cross and dot product computations to prevent resulting values from overflowing their maximum size in a processor performing the operations.

Processing logic may then determine a voltage to be applied to the motion generating mechanism based on the determined movement (processing block 606). Once the desired joint velocities are determined, processing logic may generate motion generation mechanism voltages (e.g., actuator/motor voltages) that will produce these joint velocities. From motor equation V=$K_E$ω+T/$K_E$*R, it can be seen that the voltage has a velocity dependent ($K_E$ω) term as well as a torque dependent (T/$K_E$*R) term. With a high-torque or high-gear reduction (large $K_e$) motor, it may suffice to simply neglect the torque term, and use the resulting control rule V=$K_E$ω. In one embodiment, for better response, the inertial effects or other known characteristics of the motor can be taken into account. For example, assuming the motor has rotational inertia I, the torque due to changes in angular velocity may be expressed as $$T = J\frac{d}{dt}\omega.$$

Using this leads to a control rule for calculating a specific motion generating mechanisms voltage as $$V = K_e\omega + \frac{JR}{K_e} \cdot \frac{d}{dt}\omega.$$

In one embodiment, by compensating for motor inertia, there may be less lag in responding to fast movements.

Processing logic then drives the motion generating mechanism with the determined voltage to move the component of the handheld tool in the determined direction of movement towards the desired orientation (processing block 608). As discussed herein, the handheld tool may include two or more motion generating mechanisms that move the component/implement in different degrees of freedom. In one embodiment, the voltages applied to each motion generating mechanism represent their respective motions (e.g., proportional speed, direction, acceleration, etc.) to obtain the desired orientation.

In one embodiment, the measurement of the component's orientation is performed on a periodic basis, such somewhere in the range of 30-500 times per second, and the motion generating mechanism is driven a corresponding number of times per second. The periodic measurement and driving of the motion generating mechanism may continually update the position of the component/implement during use and movement by a user. Furthermore, because the dot and cross products are utilized and can employ fixed-point calculations, this heuristic for controlling movement of components of the handheld tool in three dimensions may be very computationally inexpensive. For example, the cross product uses 6 multiplications and 3 additions, and the dot product uses 3 multiplications and 2 additions. This makes the use of fixed-point computations convenient, which is much faster on processors without a floating-point unit.

As discussed above, because the sensor measurements are collected periodically, and the motion control is performed from the sensor measurements without additional sensors (e.g., joint position sensors), the different components (e.g., implement and housing) may drift away from an expected orientation over time due to very small errors inherent in the motor command calculations. That is very small errors from an initial known orientation can be introduced, and over several minutes of use of the handheld tool, can result in severe misalignment. Therefore, in one embodiment, the alignment of the different parts of the handheld tool is maintained from the sensor measurements, and is performed while the orientation control discussed above is being performed.

Figure 7:
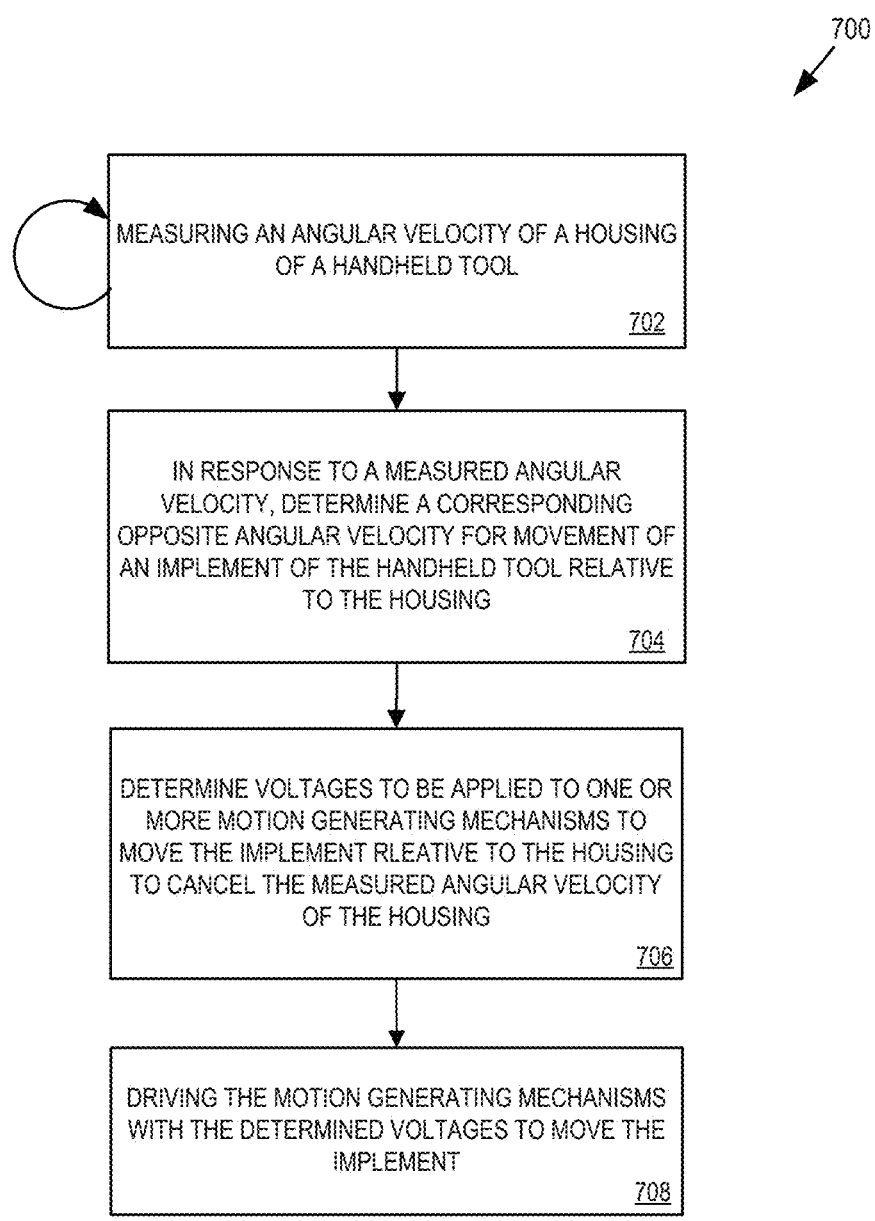
FIG. 7 is a flow chart illustrating a process for controlling stabilization of a handheld tool to correct for disturbance motions, in accordance with an embodiment of the disclosure.

FIG. 7 is a flow chart illustrating a process for controlling stabilization of a handheld tool to correct for disturbance motions, in accordance with an embodiment of the disclosure. The process 700 may be performed by processing logic that may comprise hardware (circuitry, dedicated logic, etc.), software (such as is run on a general purpose computer system or a dedicated machine), firmware, or a combination. In one embodiment, the process is performed by a feed forward controller (e.g., feed forward controller 410). Furthermore, the order in which some or all of the process blocks appear in process 700 should not be deemed limiting. Rather, one of ordinary skill in the art having the benefit of the present disclosure will understand that some of the process blocks may be executed in a variety of orders not illustrated, or even in parallel.

Processing logic may begin by measuring an angular velocity of a housing of a handheld tool (processing block 702). In one embodiment, as discussed above in FIG. 1, a housing of a handheld tool can include a sensor, such as an IMU. The IMU can take direct measurements of the angular velocity of the housing during use of the handheld tool. If a user rotates the housing of the handheld tool (e.g., relative to Earth's gravitational force), for the implement of the handheld tool to avoid a corresponding rotation relative to earth, an opposite and corresponding rotation of the implement relative to the handle with the opposite angular velocity is determined by processing logic (processing block 704). This opposite angular velocity, in one embodiment, can be expressed as a vector. Processing logic, when determining the opposite and corresponding rotation of the implement uses the vector to compute dot products against vectors representing each of the motion generating mechanisms rotational axis. These dot products represent the angular velocities at each motion generating mechanism that would cancel the handle's angular rotational movement.

Processing logic may determine voltages to be applied to one or more motion generating mechanisms to move the implement relative to the housing to cancel angular movement of the housing (processing block 706). As discussed above, the angular velocities determined at processing block 704 can be used to derive motion generating mechanism voltages as discussed above. Processing logic may then drive the motion generating mechanisms with the determined voltages to move the implement (processing block 708).

In one embodiment, stabilization of an implement of a handheld tool may be greatly improved by the use of a feedforward controller, such as feed forward controller 410 discussed above in of FIG. 4, and using the processing logic of FIG. 7. In one embodiment, the feed forward controller is an angular velocity feed forward controller than may operate in parallel with the stabilization technique discussed above in FIG. 5. By adding the feedforward controller 410 to the triple product calculator 408 and stabilization controller 402 discussed above in FIG. 4, an improved control technique is produced. In embodiments, for example, the feedforward controller can provide motor commands (e.g., voltages) that cancel the majority of disturbance motions due to unintentional rotations, while the stabilization controller can provide motor commands (e.g., voltages) that correct the remaining error caused by unintentional user movements while using a handheld tool. By adding these two sets of motor commands together, the combined voltages accurately cancel the unintentional user motions.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

The following statements provide general expressions of the disclosure herein:

A. A handheld tool, comprising:
a housing having a first inertial measuring unit ("IMU") that measures at least an orientation of the housing;
a first motion generating mechanism disposed within the housing;
an attachment arm having a second IMU that measures at least an orientation of the attachment arm, wherein the attachment arm extends from the housing and is coupled with the first motion-generating mechanism;
a second motion generating mechanism disposed within the attachment arm;
a user-assistive device attached to a distal end of the attachment arm; and
a tremor tracking module ("TTM") attached to the housing that, based on the measured orientation of the housing and the measured orientation of the attachment arm, controls the first motion generating mechanism and the second motion generating mechanism to move the attachment arm relative to the housing to stabilize motion of the user-assistive device.

B. The handheld tool of statement A, further comprising a controller coupled to the TTM to:
read the measured orientation of the housing and the measured orientation of the attachment arm,
based on a desired orientation of the user-assistive device, generate first and second motor commands including at least a direction and a speed of movement of the first motion generating mechanism and the second motion generating mechanism, respectively, that will move the attachment arm from the measured orientation to the desired orientation; and
drive each of the first motion generating mechanism and the second motion generating mechanism with the first and second motor commands.

C. The handheld tool of statement B, wherein the first and second motor commands comprise voltages that are applied to the first motion generating mechanism and the second motion generating mechanism, respectively, to control one or more of an acceleration, a speed, and a direction of movement of the respective the first motion generating mechanism and the second motion generating mechanism.

D. The handheld tool of statement B or C, wherein the desired orientation comprises an expected orientation of the attachment arm relative to the housing.

E. The handheld tool of statement D, further comprising the controller to:
based on the expected orientation of the housing relative to the user-assistive device, determine a misalignment error of the housing and the user assistive device as a result of sensor drift from one or more shared orientation axes of the housing, the attachment arm, and the user assistive device; and
correct the misalignment error prior to generation of the first and second motor commands.

F. The handheld tool of any one of statements B to E, further comprising:
the first IMU to measure an angular velocity of the housing of the handheld tool, wherein the measured angular velocity is indicative of a disturbance motion of the user-assistive device; and
the controller to:
determine third and fourth motor commands providing corresponding opposite angular velocities to the first motion generating mechanism and the second motion generating mechanism, respectively, that cancel the angular velocity of the housing,
add the first and third motor commands to obtain a fifth motor command for driving the first motion generating mechanism,
add the second and fourth motor commands to obtain an sixth motor command for driving the second motion generating mechanism, and
drive each of the first motion generating mechanism and the second motion generating mechanism with the fifth and sixth motor commands.

G. The handheld tool of any one of statements B to F, wherein the orientation of the housing and the measured orientation of the attachment arm are periodically measured by their respective IMUs, and the first motion generating mechanism and the second motion generating mechanism are driven with motor commands for each corresponding periodic measurement.

H. The handheld tool of any one of statements A to G, wherein the first motion generating mechanism moves the user-assistive device in a first degree of freedom relative to the housing, and the second motion generating mechanism moves the user-assistive device in a second degree of freedom relative to the housing.

I. The handheld tool of any one of statements A to H, wherein the first IMU and the second IMU are each six degree of freedom IMUs having at least an accelerometer and a gyroscope.

J. The handheld tool of any one of statements A to I, wherein the user-assistive device comprises any of a manufacturing tool, a surgical tool, a kitchen utensil, a sporting tool, a yard tool, a grooming utensil, or a dental hygiene tool.

K. The handheld tool of any one of statements A to J, further comprising:
a memory unit coupled to the TTM; and
logic executable by the controller that when executed by the controller causes the handheld tool to perform operations comprising:
generating a motion log within the memory unit based upon the detected motion while a user is holding the handheld tool; and
periodically communicating the motion log to a remote server.

L. A method performed by a handheld tool, the method comprising:
measuring, with a first inertial measuring unit ("IMU"), at least an orientation of a housing of a handheld tool;
measuring, with a second IMU, at least an orientation or an attachment arm extending from the housing of the handheld tool;
storing the orientation of the housing and the orientation of the attachment arm in a memory; and
controlling, with a processing logic, a first motion generating mechanism and a second motion generating mechanism to move the attachment arm relative to the housing based on the measured orientation of the housing and the measured orientation of the attachment arm to stabilize motion of a user-assistive device attached to a distal end of the attachment arm.

M. The method of statement L, wherein the first IMU and the second IMU are each six degree of freedom IMUs having at least an accelerometer and a gyroscope.

N. The method of statement L or M, further comprising:
reading the measured orientation of the housing and the measured orientation of the attachment arm,
based on a desired orientation of the user-assistive device, generating first and second motor commands including at least a direction and a speed of movement of the first motion generating mechanism and the second motion generating mechanism, respectively, that will move the attachment arm from the measured orientation to the desired orientation; and driving each of the first motion generating mechanism and the second motion generating mechanism with the first and second motor commands O. The method of statement N, further comprising:

based on the expected orientation of the housing relative to the user-assistive device, determining a misalignment error of the housing and the user assistive device as a result of sensor drift from one or more shared orientation axes of the housing, the attachment arm, and the user assistive device; and correcting the misalignment error prior to generation of the first and second motor commands.

P. The method of statement N or O, further comprising:

measuring, with the first IMU, an angular velocity of the housing of the handheld tool, wherein the measured angular velocity is indicative of a disturbance motion of the user-assistive device;

determining third and fourth motor commands providing corresponding opposite angular velocities to the first motion generating mechanism and the second motion generating mechanism, respectively, that cancel the angular velocity of the housing;

adding the first and third motor commands to obtain a fifth motor command for driving the first motion generating mechanism;

adding the second and fourth motor commands to obtain an sixth motor command for driving the second motion generating mechanism; and driving each of the first motion generating mechanism and the second motion generating mechanism with the fifth and sixth motor commands.

Q. A non-transitory machine readable storage medium having instructions stored thereon, which when executed by a processing system, cause the processing system to perform a method comprising:

measuring, with a first inertial measuring unit ("IMU"), at least an orientation of a housing of a handheld tool;

measuring, with a second IMU, at least an orientation or an attachment arm extending from the housing of the handheld tool;

storing the orientation of the housing and the orientation of the attachment arm in a memory; and controlling, with a processing logic, a first motion generating mechanism and a second motion generating mechanism to move the attachment arm relative to the housing based on the measured orientation of the housing and the measured orientation of the attachment arm to stabilize motion of a user-assistive device attached to a distal end of the attachment arm.

R. The non-transitory machine readable storage medium of statement Q, wherein the first IMU and the second IMU are each six degree of freedom IMUs having at least an accelerometer and a gyroscope.

S. The non-transitory machine readable storage medium of statement Q or R, further comprising:

reading the measured orientation of the housing and the measured orientation of the attachment arm, based on a desired orientation of the user-assistive device, generating first and second motor commands including at least a direction and a speed of movement of the first motion generating mechanism and the second motion generating mechanism, respectively, that will move the attachment arm from the measured orientation to the desired orientation; and driving each of the first motion generating mechanism and the second motion generating mechanism with the first and second motor commands T. The non-transitory machine readable storage medium of statement S, further comprising:

based on the expected orientation of the housing relative to the user-assistive device, determining a misalignment error of the housing and the user assistive device as a result of sensor drift from one or more shared orientation axes of the housing, the attachment arm, and the user assistive device; and correcting the misalignment error prior to generation of the first and second motor commands.

U. The non-transitory machine readable storage medium of statement S or T, further comprising:

measuring, with the first IMU, an angular velocity of the housing of the handheld tool, wherein the measured angular velocity is indicative of a disturbance motion of the user-assistive device;

determining third and fourth motor commands providing corresponding opposite angular velocities to the first motion generating mechanism and the second motion generating mechanism, respectively, that cancel the angular velocity of the housing;

adding the first and third motor commands to obtain a fifth motor command for driving the first motion generating mechanism;

adding the second and fourth motor commands to obtain an sixth motor command for driving the second motion generating mechanism; and driving each of the first motion generating mechanism and the second motion generating mechanism with the fifth and sixth motor commands.

What is claimed is:

1. A handheld tool, comprising:
a housing having a first inertial measuring unit ("IMU") that measures at least an orientation of the housing relative to a reference frame of Earth;
a first motion generating mechanism disposed within the housing;
an attachment arm having a second IMU disposed on the attachment arm and configured to measure at least an orientation of the attachment arm relative to the reference frame of Earth, wherein the attachment arm extends from the housing and is coupled with the first motion-generating mechanism;
a second motion generating mechanism coupled with the first motion-generating mechanism to collectively move a user-assistive device attached to a distal end of the attachment arm; and
a controller disposed within the housing and coupled to the first and second IMUs and the first and second motion-generating mechanisms, the controller including logic configured to:
based on the measured orientation of the housing and the measured orientation of the attachment arm, control the first motion generating mechanism and the second motion generating mechanism to move the attachment arm relative to the housing to stabilize motion of the user-assistive device;
when one or more shared orientation axes of the housing, the attachment arm, or the user assistive device are measured as misaligned, determine that a misalignment error has resulted from sensor drift, wherein the one or more shared orientation axes comprise axes of components, including the housing, the attachment arm, or the user assistive device, that are physically constant relative to each other despite the components moving relative to each other along other axes; and correct the misalignment error prior to generating one or more motor commands for driving the first or second motion generating mechanisms.

2. The handheld tool of claim 1, wherein the controller is further configured to:

read the measured orientation of the housing and the measured orientation of the attachment arm, based on a desired orientation of the user-assistive device, generate first and second motor commands including at least a direction and a speed of movement of the first motion generating mechanism and the second motion generating mechanism, respectively, that will move the attachment arm from the measured orientation to the desired orientation; and drive each of the first motion generating mechanism and the second motion generating mechanism with the first and second motor commands.

3. The handheld tool of claim 2, wherein the first and second motor commands comprise voltages that are applied to the first motion generating mechanism and the second motion generating mechanism, respectively, to control one or more of an acceleration, a speed, and a direction of movement of the respective first motion generating mechanism and the second motion generating mechanism.

4. The handheld tool of claim 2, wherein the desired orientation comprises an expected orientation of the attachment arm relative to the housing.

5. The handheld tool of claim 2, further comprising:

the first IMU to measure an angular velocity of the housing of the handheld tool, wherein the measured angular velocity is indicative of a disturbance motion of the user-assistive device; and the controller further configured to:

determine third and fourth motor commands providing corresponding opposite angular velocities to the first motion generating mechanism and the second motion generating mechanism, respectively, that cancel the angular velocity of the housing, add the first and third motor commands to obtain a fifth motor command for driving the first motion generating mechanism, add the second and fourth motor commands to obtain an sixth motor command for driving the second motion generating mechanism, and drive each of the first motion generating mechanism and the second motion generating mechanism with the fifth and sixth motor commands.

6. The handheld tool of claim 2, wherein the orientation of the housing and the measured orientation of the attachment arm are periodically measured by their respective IMUs, and the first motion generating mechanism and the second motion generating mechanism are driven with motor commands for each corresponding periodic measurement.

7. The handheld tool of claim 1, wherein the first motion generating mechanism moves the user-assistive device in a first degree of freedom relative to the housing, and the second motion generating mechanism moves the user-assistive device in a second degree of freedom relative to the housing.

8. The handheld tool of claim 1, wherein the first IMU and the second IMU are each six degree of freedom IMUs having at least an accelerometer and a gyroscope.

9. The handheld tool of claim 1, wherein the user-assistive device comprises any of a manufacturing tool, a surgical tool, a kitchen utensil, a sporting tool, a yard tool, a grooming utensil, or a dental hygiene tool.

10. The handheld tool of claim 1, further comprising:

a memory unit coupled to the controller; and logic executable by the controller that when executed by the controller causes the handheld tool to perform operations comprising:

generating a motion log within the memory unit based upon the detected motion while a user is holding the handheld tool; and periodically communicating the motion log to a remote server.

11. A method performed by a handheld tool, the method comprising:

measuring, with a first inertial measuring unit ("IMU"), at least an orientation of a housing of a handheld tool relative to a reference frame of Earth;

measuring, with a second IMU, at least an orientation of an attachment arm relative to the reference frame of Earth, wherein the attachment arm extends from the housing of the handheld tool;

storing the orientation of the housing and the orientation of the attachment arm in a memory;

controlling, with a processing logic, a first motion generating mechanism and a second motion generating mechanism to move the attachment arm relative to the housing based on the measured orientation of the housing and the measured orientation of the attachment arm to stabilize motion of a user-assistive device attached to a distal end of the attachment arm;

when one or more shared orientation axes of the housing, the attachment arm, or a user assistive device attached to the attachment arm are measured as misaligned, determining that a misalignment error has resulted from sensor drift, wherein the one or more shared orientation axes comprise axes of components, including the housing, the attachment arm, or the user assistive device, that are physically constant relative to each other despite the components moving relative to each other along other axes; and correcting the misalignment error prior to generating one or more motor commands for driving the first or second motion generating mechanisms.

12. The method of claim 11, wherein the first IMU and the second IMU are each six degree of freedom IMUs having at least an accelerometer and a gyroscope.

13. The method of claim 11, further comprising:

reading the measured orientation of the housing and the measured orientation of the attachment arm, based on a desired orientation of the user-assistive device, generating first and second motor commands including at least a direction and a speed of movement of the first motion generating mechanism and the second motion generating mechanism, respectively, that will move the attachment arm from the measured orientation to the desired orientation; and driving each of the first motion generating mechanism and the second motion generating mechanism with the first and second motor commands.

14. The method of claim 13, further comprising:

measuring, with the first IMU, an angular velocity of the housing of the handheld tool, wherein the measured angular velocity is indicative of a disturbance motion of the user-assistive device;

determining third and fourth motor commands providing corresponding opposite angular velocities to the first motion generating mechanism and the second motion generating mechanism, respectively, that cancel the angular velocity of the housing;

adding the first and third motor commands to obtain a fifth motor command for driving the first motion generating mechanism;

adding the second and fourth motor commands to obtain an sixth motor command for driving the second motion generating mechanism; and driving each of the first motion generating mechanism and the second motion generating mechanism with the fifth and sixth motor commands.

15. A non-transitory machine readable storage medium having instructions stored thereon, which when executed by a processing system, cause the processing system to perform a method comprising:

measuring, with a first inertial measuring unit ("IMU"), at least an orientation of a housing of a handheld tool relative to a reference frame of Earth;

measuring, with a second IMU, at least an orientation of an attachment arm extending from the housing of the handheld tool relative to a reference frame of Earth;

storing the orientation of the housing and the orientation of the attachment arm in a memory;

controlling, with a processing logic, a first motion generating mechanism and a second motion generating mechanism to move the attachment arm relative to the housing based on the measured orientation of the housing and the measured orientation of the attachment arm to stabilize motion of a user-assistive device attached to a distal end of the attachment arm;

when one or more shared orientation axes of the housing, the attachment arm, or a user assistive device attached to the attachment arm are measured as misaligned, determining that a misalignment error has resulted from sensor drift, wherein the one or more shared orientation axes comprise axes of components, including the housing, the attachment arm, or the user assistive device, that are physically constant relative to each other despite the components moving relative to each other along other axes; and correcting the misalignment error prior to generating one or more motor commands for driving the first or second motion generating mechanisms.

16. The non-transitory machine readable storage medium of claim 15, wherein the first IMU and the second IMU are each six degree of freedom IMUs having at least an accelerometer and a gyroscope.

17. The non-transitory machine readable storage medium of claim 15, further comprising:

reading the measured orientation of the housing and the measured orientation of the attachment arm, based on a desired orientation of the user-assistive device, generating first and second motor commands including at least a direction and a speed of movement of the first motion generating mechanism and the second motion generating mechanism, respectively, that will move the attachment arm from the measured orientation to the desired orientation; and driving each of the first motion generating mechanism and the second motion generating mechanism with the first and second motor commands.

18. The non-transitory machine readable storage medium of claim 17, further comprising:

measuring, with the first IMU, an angular velocity of the housing of the handheld tool, wherein the measured angular velocity is indicative of a disturbance motion of the user-assistive device;

determining third and fourth motor commands providing corresponding opposite angular velocities to the first motion generating mechanism and the second motion generating mechanism, respectively, that cancel the angular velocity of the housing;

adding the first and third motor commands to obtain a fifth motor command for driving the first motion generating mechanism;

adding the second and fourth motor commands to obtain an sixth motor command for driving the second motion generating mechanism; and driving each of the first motion generating mechanism and the second motion generating mechanism with the fifth and sixth motor commands.

19. A handheld tool, comprising:

a handle including a first sensor that measures at least an orientation of the handle relative to a reference frame of Earth;

a first motion generating mechanism disposed within the handle;

an attachment arm having a second sensor disposed thereon that measures at least an orientation of the attachment arm relative to the reference frame of Earth, wherein the attachment arm extends from the handle and is coupled with the first motion-generating mechanism;

a second motion generating mechanism coupled with the first motion-generating mechanism to collectively move a user-assistive device attached to a distal end of the attachment arm in at least two degrees of freedom; and a controller coupled to the first and second sensors and the first and second motion generating mechanisms, the controller including logic that when executed causes the handheld tool to perform operations including:

measuring orientations of the housing and the attachment arm;

when one or more shared orientation axes of the housing, the attachment arm, or the user assistive device are measured as misaligned, determining that a misalignment error has resulted from sensor drift, wherein the one or more shared orientation axes comprise axes of components, including the housing, the attachment arm, or the user assistive device, that are physically constant relative to each other despite the components moving relative to each other along other axes; and correcting the misalignment error prior to generating one or more motor commands for driving the first or second motion generating mechanisms.

20. The handheld tool of claim 1, wherein the first and second IMUs each include an accelerometer and a gyroscope to measure the orientation of the housing and the orientation of the attachment arm, respectively, relative to the reference frame of Earth.

* * * * *